(12) United States Patent
Weirich et al.

(10) Patent No.: US 8,162,984 B2
(45) Date of Patent: Apr. 24, 2012

(54) FORCED GROWTH AXIAL GROWING SPINE DEVICE

(75) Inventors: Caroline Weirich, Arlington, VA (US); Kevin R. Strauss, Leesburg, VA (US); Larry McClintock, Gore, VA (US)

(73) Assignee: K2M, Inc., Leesburg, VA (US)

( * ) Notice: Subject to any disclaimer, the term of this patent is extended or adjusted under 35 U.S.C. 154(b) by 161 days.

(21) Appl. No.: 12/710,029

(22) Filed: Feb. 22, 2010

(65) Prior Publication Data

US 2010/0217323 A1 Aug. 26, 2010

Related U.S. Application Data

(60) Provisional application No. 61/154,041, filed on Feb. 20, 2009.

(51) Int. Cl.
*A61B 17/70* (2006.01)
(52) U.S. Cl. ..................................... 606/256
(58) Field of Classification Search ............. 606/53–58, 606/250–262, 278, 279, 282, 320
See application file for complete search history.

(56) References Cited

U.S. PATENT DOCUMENTS

| | | |
|---|---|---|
| 4,567,884 A | 2/1986 | Edwards |
| 4,929,247 A | 5/1990 | Rayhack |
| 5,281,222 A | 1/1994 | Allard et al. |
| 5,330,473 A | 7/1994 | Howland |
| 5,380,323 A | 1/1995 | Howland |
| 5,451,226 A | 9/1995 | Pfeil et al. |
| 5,466,261 A | 11/1995 | Richelsoph |
| 5,630,816 A | 5/1997 | Kambin |
| 5,720,746 A | 2/1998 | Soubeiran |
| 5,766,173 A | 6/1998 | Ross, Jr. et al. |
| 5,947,966 A | 9/1999 | Drewry et al. |
| 6,136,000 A | 10/2000 | Louis et al. |
| 6,136,003 A | 10/2000 | Hoeck et al. |
| 6,277,119 B1 | 8/2001 | Walulik et al. |
| 6,402,751 B1 | 6/2002 | Hoeck et al. |
| 6,602,253 B2 | 8/2003 | Richelsoph et al. |
| 6,616,664 B2 | 9/2003 | Walulik et al. |
| 6,918,910 B2 | 7/2005 | Smith et al. |
| 6,991,632 B2 | 1/2006 | Ritland |
| 7,004,943 B2 | 2/2006 | Ferrante et al. |
| 7,029,472 B1 * | 4/2006 | Fortin ............................. 606/60 |
| 7,029,474 B2 | 4/2006 | Richelsoph et al. |
| 7,214,226 B2 * | 5/2007 | Alleyne ..................... 606/86 A |
| 7,927,357 B2 * | 4/2011 | Sacher et al. ................. 606/258 |
| 2004/0193266 A1 | 9/2004 | Meyer |
| 2005/0171543 A1 | 8/2005 | Timm et al. |
| 2005/0228378 A1 | 10/2005 | Kalfas et al. |
| 2005/0246034 A1 | 11/2005 | Soubeiran |

(Continued)

*Primary Examiner* — Pedro Philogene
(74) *Attorney, Agent, or Firm* — Carter, DeLuca, Farrell & Schmidt, LLP

(57) ABSTRACT

A forced growth axial growing spine device includes a central body portion having opposing ends. At least one housing is disposed at one end of the central body portion. The at least one housing includes a locking mechanism. At least one rigid member is coupled to the central body portion. The locking mechanism allows the rigid member to translate in one direction and inhibits translation of the rigid member in an opposing direction. Additionally, the central body portion includes a cam and at least one port. One or more ball bearings may be inserted into the ports. Operation of the cam in conjunction with the ball bearing urges the rigid member away from the cam, thereby increasing an overall length of the forced growth axial growing spine device.

19 Claims, 8 Drawing Sheets

U.S. PATENT DOCUMENTS

| | | |
|---|---|---|
| 2005/0261779 A1 | 11/2005 | Meyer |
| 2006/0009767 A1 | 1/2006 | Kiester |
| 2006/0079892 A1 | 4/2006 | Roychowdhury et al. |
| 2006/0155279 A1 | 7/2006 | Ogilvie |
| 2006/0195087 A1 | 8/2006 | Sacher et al. |
| 2006/0195088 A1 | 8/2006 | Sacher et al. |
| 2006/0233597 A1 | 10/2006 | Ensign et al. |
| 2007/0173837 A1 | 7/2007 | Chan et al. |
| 2007/0191845 A1 | 8/2007 | Justis et al. |
| 2007/0233070 A1 | 10/2007 | Young |
| 2007/0282339 A1 | 12/2007 | Schwab |
| 2008/0027436 A1 | 1/2008 | Cournoyer et al. |
| 2008/0051788 A1 | 2/2008 | Schwab |

* cited by examiner

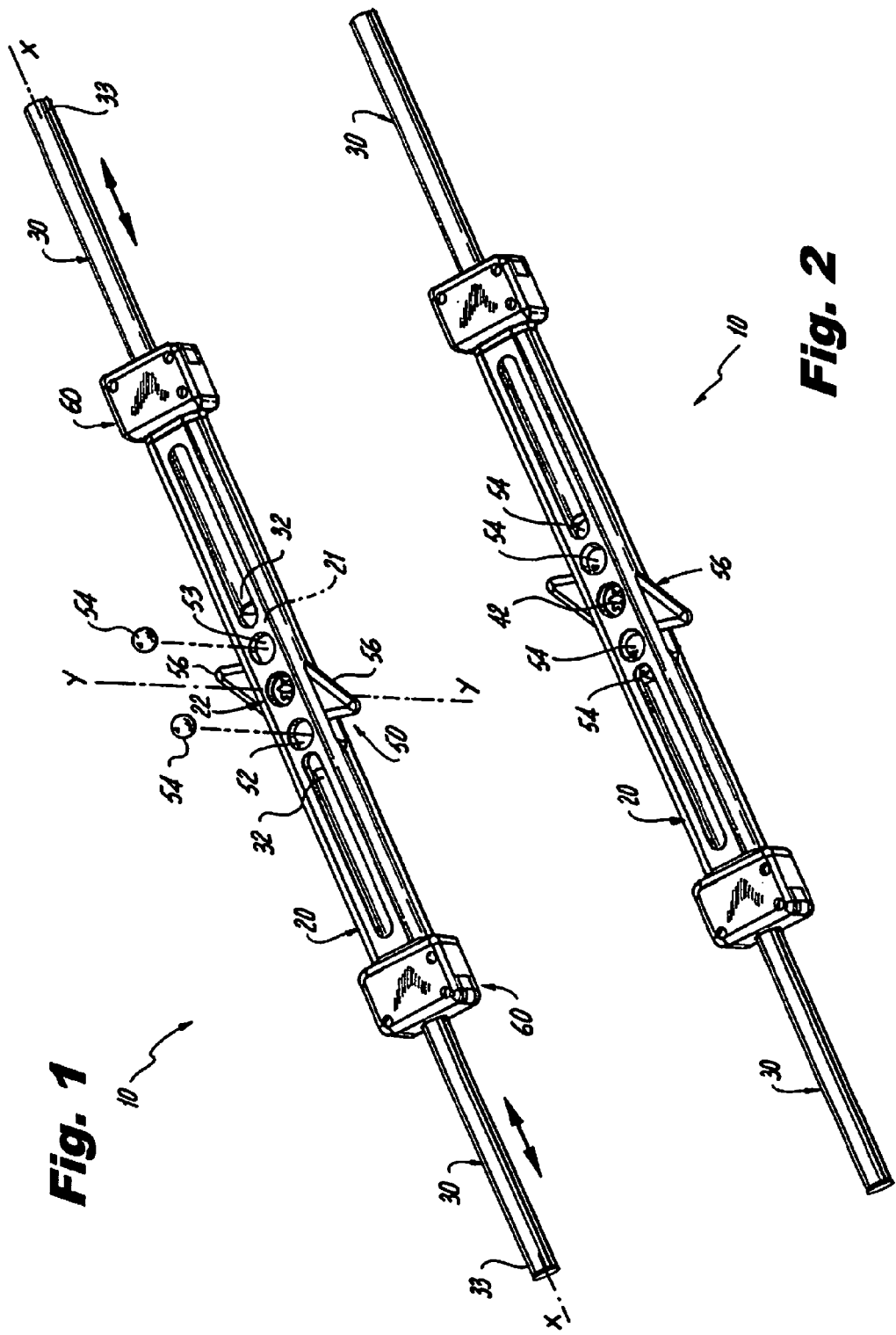

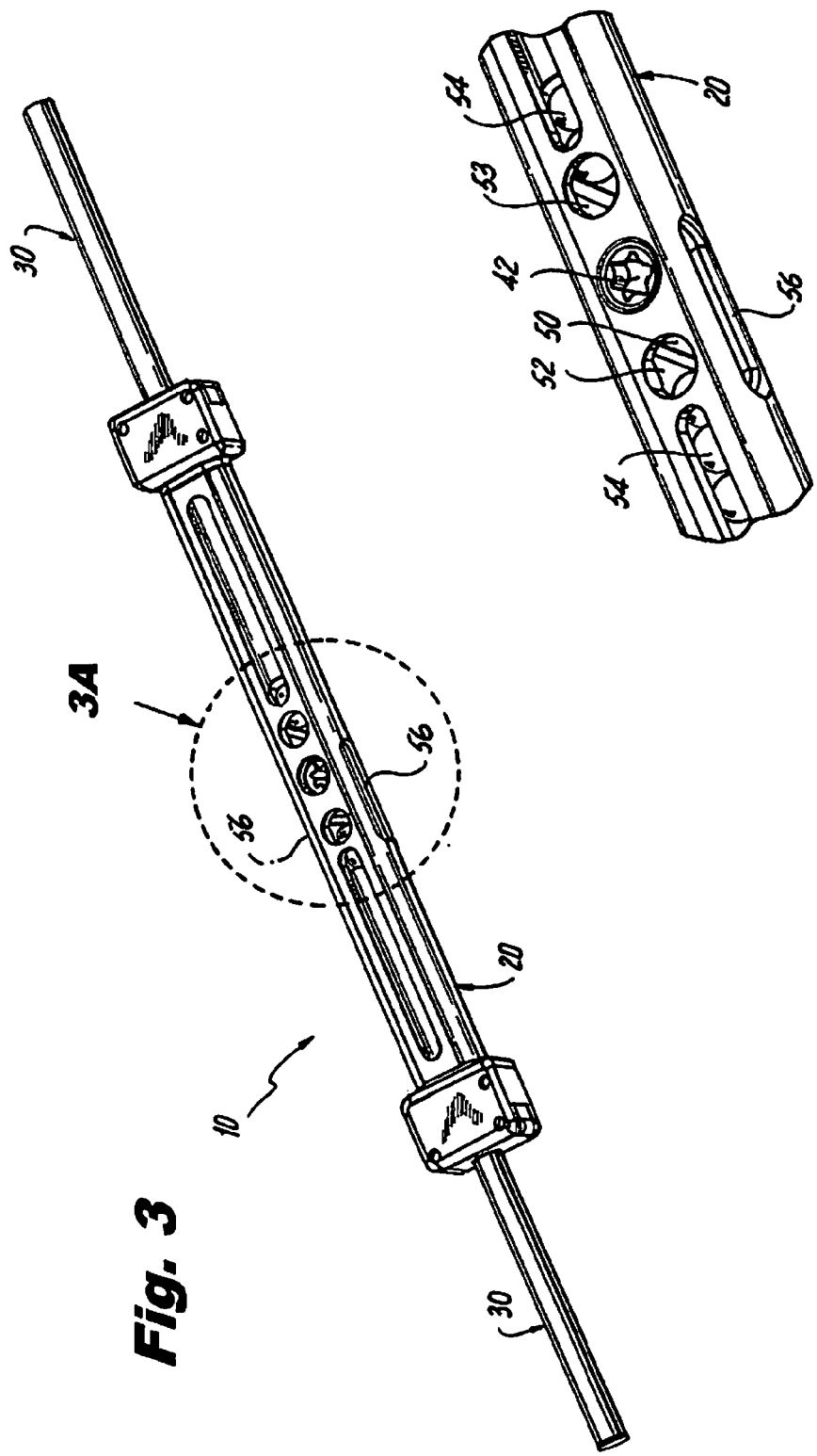

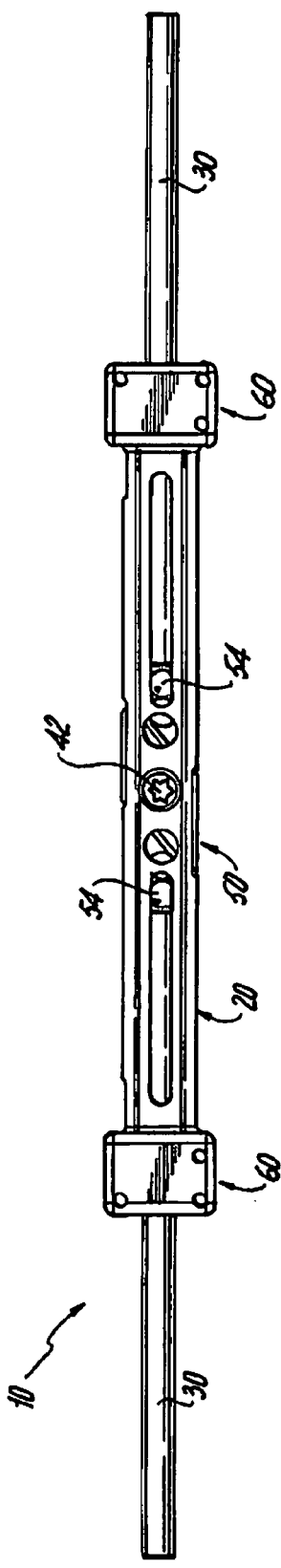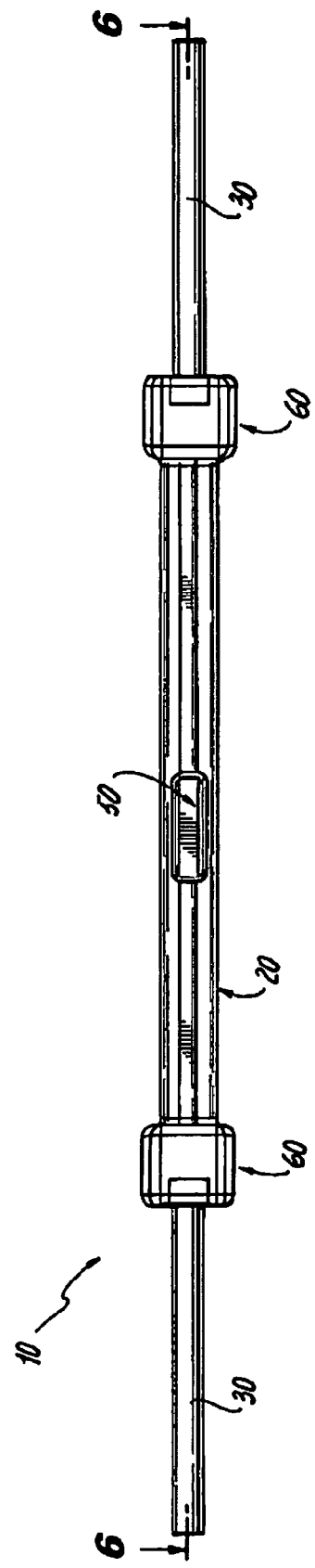

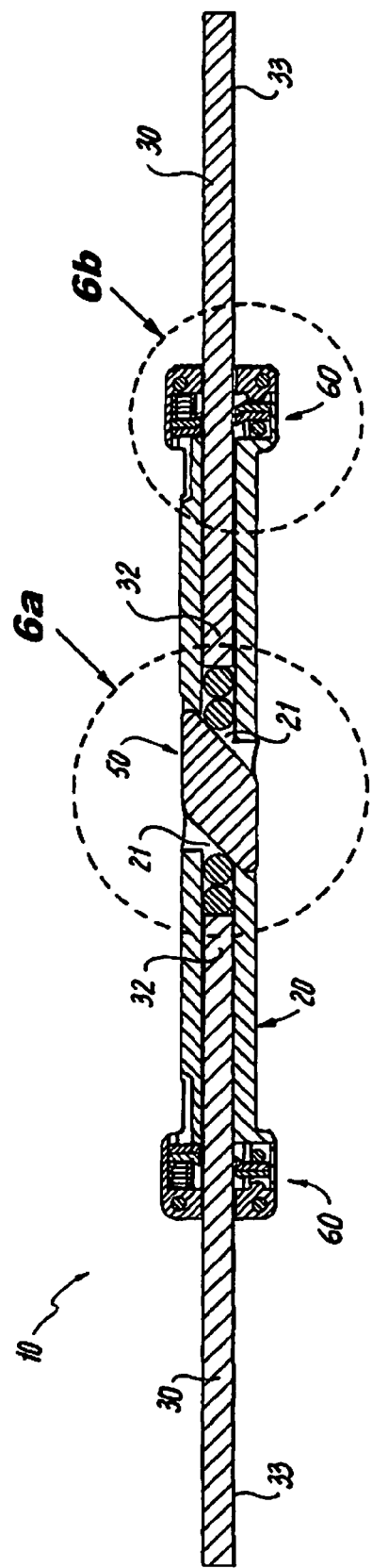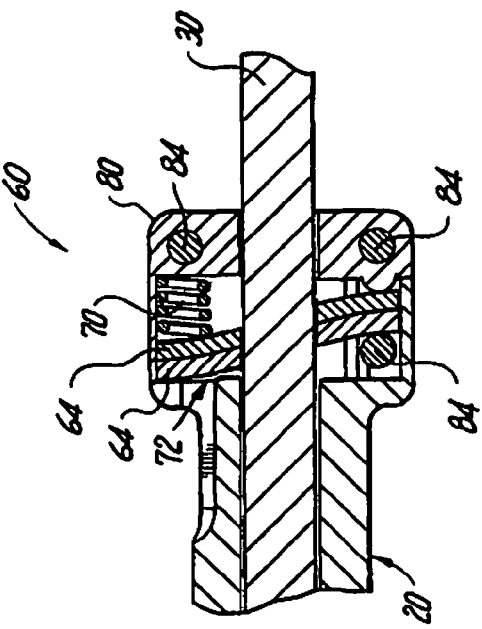
Fig. 6
Fig. 6a
Fig. 6b

FORCED GROWTH AXIAL GROWING SPINE DEVICE

CROSS-REFERENCE TO RELATED APPLICATIONS

This application claims the benefit of, and priority to, U.S. Provisional Patent Application No. 61/154,041, filed Feb. 20, 2009, the entire contents of which are incorporated by reference herein.

BACKGROUND

1. Technical Field

The present disclosure relates to devices and methods for treating spinal conditions. More particularly, the present disclosure relates to a forced growth axial growing spine device and methods of use.

2. Background of Related Art

The human spine is comprised of thirty-three vertebrae at birth and twenty-four as a mature adult. The vertebra includes the vertebral body and posterior elements, including the spinous process, transverse processes, facet joints, laminae, and pedicles. The vertebral body consists of a cortical shell surrounding a cancellous center. Between each pair of vertebrae is an intervertebral disc, which maintains the space between adjacent vertebrae and acts as a cushion under compressive, bending and rotational loads and motions. A healthy intervertebral disc consists mostly of water in the nucleus pulposus, which is the center portion of the disc. The water content gives the nucleus a spongy quality and allows it to absorb spinal stresses.

Scoliosis is a medical condition whereby the spine is curved from side to side or front to back and may also be rotated about its longitudinal axis. Typical treatment involves observation in order to determine the rate of progression and external bracing to help ensure any future growth of the spine follows the desired path and orientation.

Surgical intervention is warranted when the likelihood of curve or rotation progression is high or if a significant amount of pain or other general health risks are experienced. In these instances, a spinal fusion of various segments may be performed in order to stabilize the scoliotic curve. In younger patients, performing a spinal fusion is less desirable since it will interfere with the normal growth of the individual.

In an effort to maintain normal growth or height, while correcting a younger patient's abnormally curved spine, devices known as "growing spinal rods" have been developed. Growing spinal rods provide structure, stability, and correction to the spine, but also allow the spinal rod to lengthen without the need for replacing or adding devices to the original construct.

A major disadvantage of the current growing spinal rod systems on the market today is they require a surgical procedure for manually increasing the length of the spinal rod, usually by loosening one or more set screws, providing distraction between two spinal rod segments and then re-tightening. One system that works this way is the ISOLA® Spine System by Depuy Spine, Inc. Systems such as this require a surgical procedure approximately every six months for several years.

Another conceptual device has been proposed whereby a second device is used, in a minimally invasive fashion, to cause the spinal rod or construct to lengthen when an operator uses an instrument to actuate the device. This type of manual, or forced, growth has been developed in an effort to promote or accelerate growth.

Therefore, a need exists for a device that allows for skeletal growth and more specifically, spine growth, in a natural way and without intervention. Additionally, a need exists for the same device to be manually distracted in order to promote growth while maintaining structure and stability and can be performed in a minimally invasive procedure.

SUMMARY

In one embodiment of the present disclosure, a forced growth axial growing spine device includes a central body portion and a pair of spinal rods extending therefrom. The central body portion includes an expansion control mechanism having a rotatable cam operatively coupled to a key that is rotatable about an axis. On opposing sides of the cam is a pair of ports for receiving ball bearings or other structures for interfacing with the spinal rods. The cam may include a hexagonal or other geometrically shaped recess for receipt of a tool. On opposing ends of the central body portion are locking mechanisms that permit the spinal rods to move in a direction that is away from the centrally positioned cam, while inhibiting movement of the spinal rods in a direction that is towards the centrally located cam.

BRIEF DESCRIPTION OF THE DRAWINGS

Embodiments of the presently disclosed forced growth axial growing spine device are described herein with reference to the accompanying drawings, wherein:

FIG. 1 is a top perspective view of a forced growth axial growing spine device and ball bearings illustrating a key in an unlocked position;

FIG. 2 is a top perspective view of the forced growth axial growing spine device of FIG. 1 with the ball bearings adjacent to the spinal rod sections;

FIG. 3 is a top perspective view of the forced growth axial growing spine device of FIG. 1 with the key in a locked position;

FIG. 3A is an enlarged view of area 3A of FIG. 3;

FIG. 4 is a top plan view of the forced growth axial growing spine device of FIG. 2;

FIG. 5 is a side view of the forced growth axial growing spine device of FIG. 4;

FIG. 6 is a side cross-sectional view of the forced growth axial growing spine device of FIG. 5 taken along section line C-C;

FIG. 6a is an enlarged view of area 6a of FIG. 6 with spinal rods;

FIG. 6b is an enlarged view of area 6b of FIG. 6 with ball bearings and spinal rods;

Figure 7:
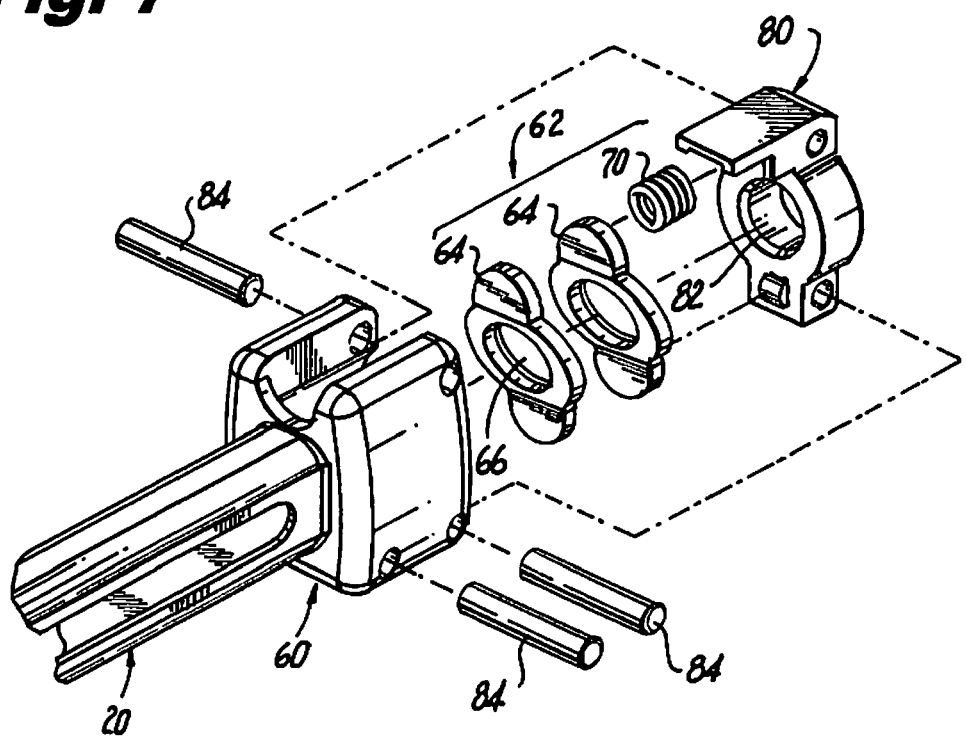
FIG. 7 is an exploded view of the housing in accordance with FIGS. 1-6B.

Other features of the present disclosure will become apparent from the following detailed description, taken in conjunction with the accompanying drawings, which illustrate, by way of example, the principles of the present disclosure.

DETAILED DESCRIPTION

Embodiments of the presently disclosed forced growth axial growing spine device will now be described in detail with reference to the drawings, wherein like reference numerals identify similar or identical elements. In the drawings and in the description that follows, the term "proximal," will refer to the end of a device or system that is closest to the operator, while the term "distal" will refer to the end of the device or system that is farthest from the operator. In addition, the term "cephalad" is used in this application to indicate a direction toward a patient's head, whereas the term "caudad" indicates a direction toward the patient's feet. Further still, for the purposes of this application, the term "medial" indicates a direction toward the middle of the body of the patient, whilst the term "lateral" indicates a direction toward a side of the body of the patient (i.e., away from the middle of the body of the patient). The term "posterior" indicates a direction toward the patient's back, and the term "anterior" indicates a direction toward the patient's front.

According to a first embodiment of the present disclosure, a forced growth axial growing spine device or axial growth device 10 will be described with reference to FIGS. 1-8. The axial growth device 10 is a natural and manual skeletal lengthening and fixation device. With reference to FIG. 1, the axial growth device 10 includes a central body portion 20 coupled with at least one rigid member. The at least one rigid member may be in the form of one or more spinal rods 30. As shown in FIG. 6, the central body portion 20 has a center passage 21 for extending two spinal rods 30 therethrough. The center passage 21 defines a longitudinal axis 'x'-'x'.

In one embodiment, the central body portion 20 is a single unit containing a center located camming mechanism 50. As shown in FIG. 1, the camming mechanism 50 is rotatable about a center point 22 defining a rotational axis 'y'-'y'. The rotational axis 'y'-'y' is perpendicular to the longitudinal axis 'x'-'x'. As shown in FIGS. 1, 2, 6, and 6A, the camming mechanism 50 has a diamond shape. The diamond shape allows the arms 56 to fit flush within the central body portion 20 in a first position, as shown in FIG. 3, and extend radially from the central body portion 20 in a second position, as shown in FIGS. 1 and 2. As a result, the arms 56 can be rotated into and out of the center passage 21.

Although a diamond shaped camming mechanism is shown, other shapes and/or configurations are contemplated. Further still, although the illustrated exemplary embodiment includes two spinal rods 35 and two housings 60, it is contemplated that a single spinal rod and a single housing 60 may be used. It is also contemplated that the disclosed axial growth device would include a first spine rod 35 disposed in one housing 60 at one end of the axial growth device 10 and a second spine 35 fixedly attached to an opposing end of the axial growth device 10.

A first port 52 and a second port 53 are juxtaposed along the longitudinal axis 'x'-'x' on opposite sides of the camming mechanism 50, and extend into the center passage 21 from only one side of the central body portion 20. The ports 52, 53 are located at a distance close enough to the camming mechanism 50 to allow the camming mechanism 50 to close or block access to the center passage 21 from each of the ports 52, 53, while the camming mechanism 50 is in the first position. The ports 52, 53 are located at a distance far enough from the camming mechanism 50 to allow the camming mechanism 50 to be rotated away from or open access to the center passage 21 from each of the ports 52, 53, while the camming mechanism 50 is in the second position. Each of the two ports 52, 53 are sized to accept and allow a ball bearings 54 or another similarly functioning spacer to pass into and be entirely located within the central passage 21. While the ball bearing 54 is in the central passage 21, the ball bearing 54 is located between the spinal rods 30 and the camming mechanism 50.

With reference to FIGS. 6, 6B, 7, and 8, a housing 60 is located at each of the opposing ends of the central body portion 20. Each of the housings 60 contains a locking mechanism 62.

As seen in FIG. 7, the locking mechanism 62 includes one or more ring plates 64, each having a hole 66 therethrough. The hole 66 has a constant inner diameter that is slightly larger than the diameter of the spinal rod 30. A pre-tensioning device 70, such as a spring, is positioned adjacent the ring plates 64 and provide a constant force against the ring plates 64, thus causing the ring plates 64 to rotate away from a perpendicular orientation with respect to the longitudinal axis 'x'-'x'. The ring plates 64 are held within the housing 60 by an end cap 80 that includes an aperture 82. The aperture 82 is sized to be slightly larger than the diameter of the spinal rod 30. The center passage 21, the hole 66, and the aperture 82 are aligned such that the spinal rod 30 may be positioned within and extend through the center passage 21, the hole 66, and the aperture 82. The end cap 80 is held to the housing 60 by a series of pins 84.

Figure 8:
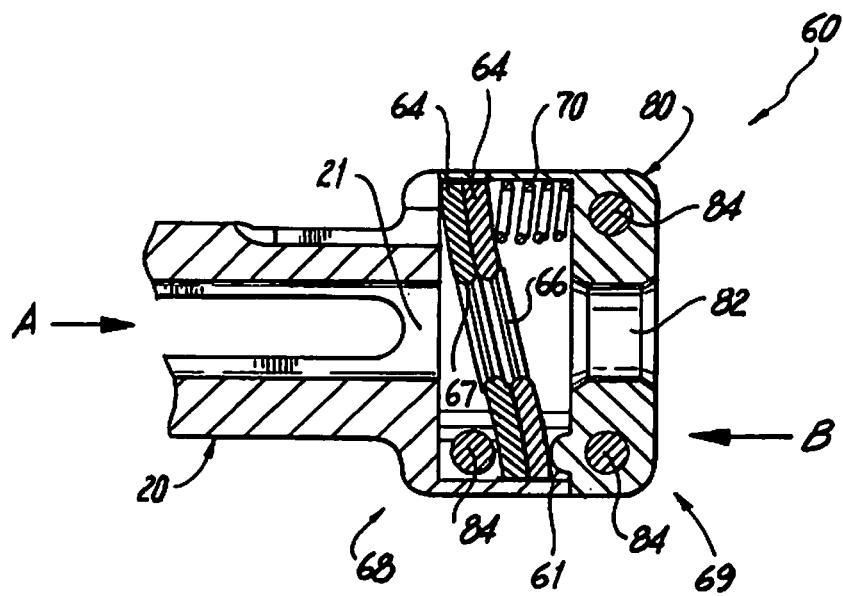
FIG. 8 is an enlarged cross-sectional view of area 6b of FIG. 6 without a spinal rod.
Figure 9:
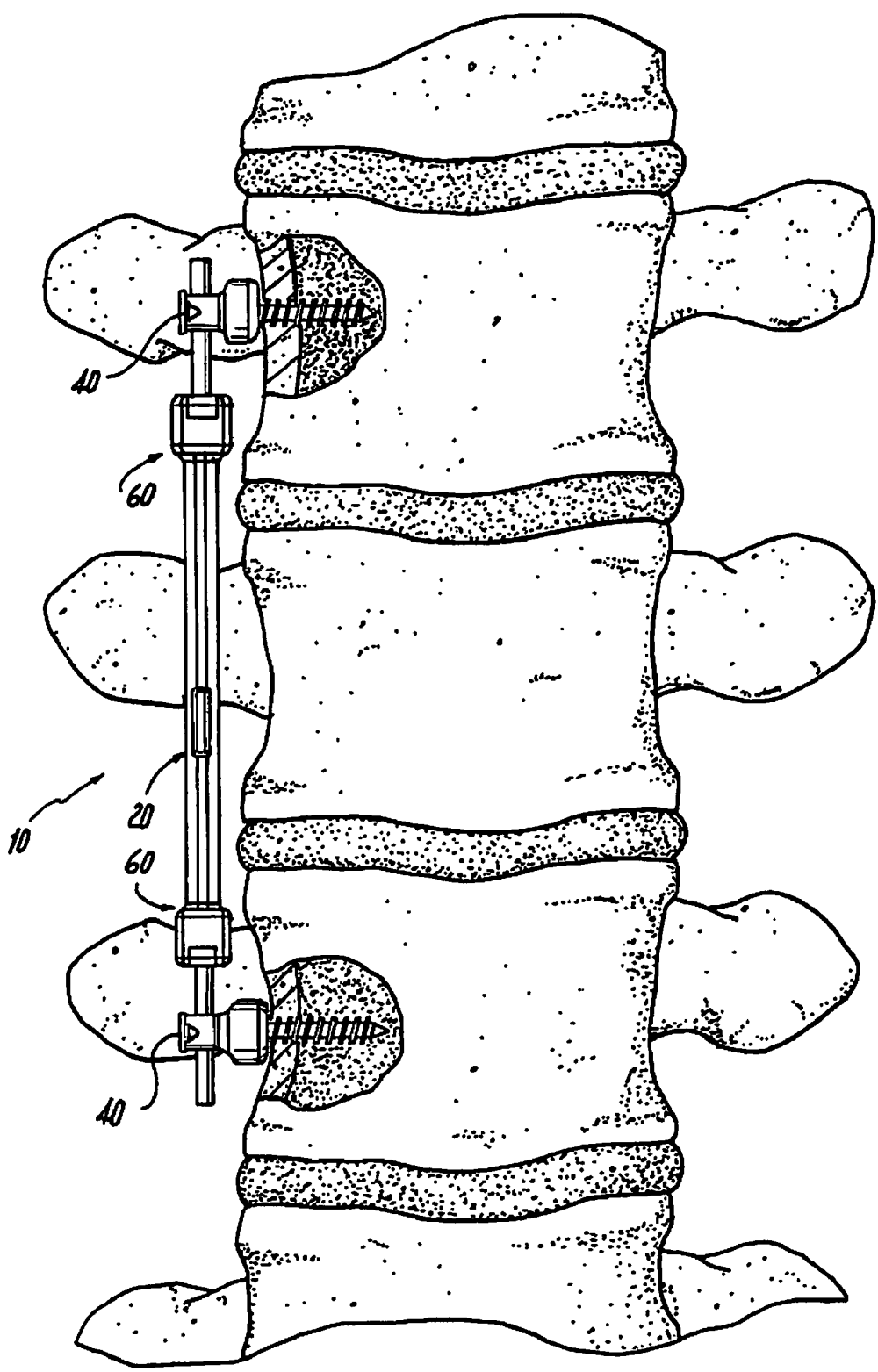
FIG. 9 is a side perspective view of the forced growth axial growing spine device of FIGS. 1-8 connected to a spinal column via pedicle screws.

As seen in FIG. 8, one side of the ring plate 64 is sandwiched between one of the pins 84 and an internal surface 61 of the housing 60. The other side of the ring plate 64 is sandwiched between an internal end 68 of the housing 60 and the spring 70, which is compressed and reacts against an external end 69 of the housing 60. As a result, a constant force is applied to the ring plate 64 by the spring 70 that causes the ring plate 64 to rotate about the pin 84. Therefore, when the spinal rod 30 is positioned through the hole 66 of the ring plates 64, an interior surface 67 of the ring plate 64, defined by the hole 66, exerts a frictional force against the spinal rod 30 that inhibits the spinal rod 30 from translating into the central passage 21.

The spinal rods 30 can be separated or extended apart from each other, thereby increasing the overall length of the axial growth device 10. Each spinal rod 30 has an internal portion 32, located within the central body portion 20, and an external portion 33, extending from the central body portion 20. The external portion 33 is lengthened by rotating or actuating the camming mechanism 50 of the axial growth device 10 to expose the ports 52, 53 to the center passage 21; inserting the ball bearings 54 or other spacers into the ports 52, 53; and then rotating or actuating the camming mechanism 50 to close the ports 52, 53, which in turn pushes the ball bearings 54 against the spinal rods 30 causing the spinal rods 30 to move further away from the camming mechanism 50. The external portion 33 of each spinal rod 30 is coupled to a vertebra by a bone anchoring device 40, such as a pedicle screw. As a result of the extending external portions 33 of the spinal rods 30, the bone anchoring devices 40 are also forced away from each other.

While at rest, the ring plates 64 are angled within the housing 60 and apply a load to the spinal rod 30. By moving the spinal rod 30, such that the spinal rod 30 applies a force to counteract the force applied by the spring element 70, (i.e., by translating spinal rod 30 in the direction of arrow A in FIG. 8) the ring plates 64 rotate to reduce the frictional force between the interior surface 67 of the hole 66 and the spinal rod 30, thus permitting translation of the spinal rod 30 therethrough.

Rotation of the ring plate 64 in the first direction A rotates the hole 66 to a substantially perpendicular position with respect to the longitudinal axis 'x'-'x', allowing unobstructed translation of the spinal rod 30 through the hole 66. Rotation in the opposite direction B rotates the ring plates 64 and hole 66 away from perpendicularity causing the interior surface 67 of the hole 66 to bind against the spinal rod 30. As a result, the spinal rod 30 is able to translate in one direction A (i.e. away from the camming mechanism 50), but not in the opposite direction B (i.e. toward the camming mechanism 50).

The spinal rods 30 are retained in position by the spring loaded ring plates 64 that create a sufficient friction interference or force against the spinal rod 30 to keep the spinal rod 30 from retracting and traversing into the central body portion 20. A more detailed description of the locking mechanism can be found in commonly owned U.S. application Ser. No. 12/368,029, filed Feb. 10, 2009, the entire contents of which are hereby incorporated by reference.

The construction of the locking mechanism 62 allows the spinal rod 30, the pedicle screw 40, and the vertebral bodies to move away from each other, while preventing unwanted movement of the components toward each other. However, a future need may exist where the opposite is desired. In this case, a release notch 72, as shown in FIG. 6B, is provided to allow unloading of the force of the spring 70 from the ring plates 64 for manual adjustment or translation of the axial growth device 10 to a new, desired position along the spinal rod 30. Should a physician desire to permit the manual translation of the spinal rod 30 in either direction, he may depress the ring plates 64, by utilizing the release notch 72, in the housing 60.

It is contemplated that the ball bearings 54 may be replaced by square blocks and that multiple spacers may be juxtaposed within the central passage 21.

Figure 10:
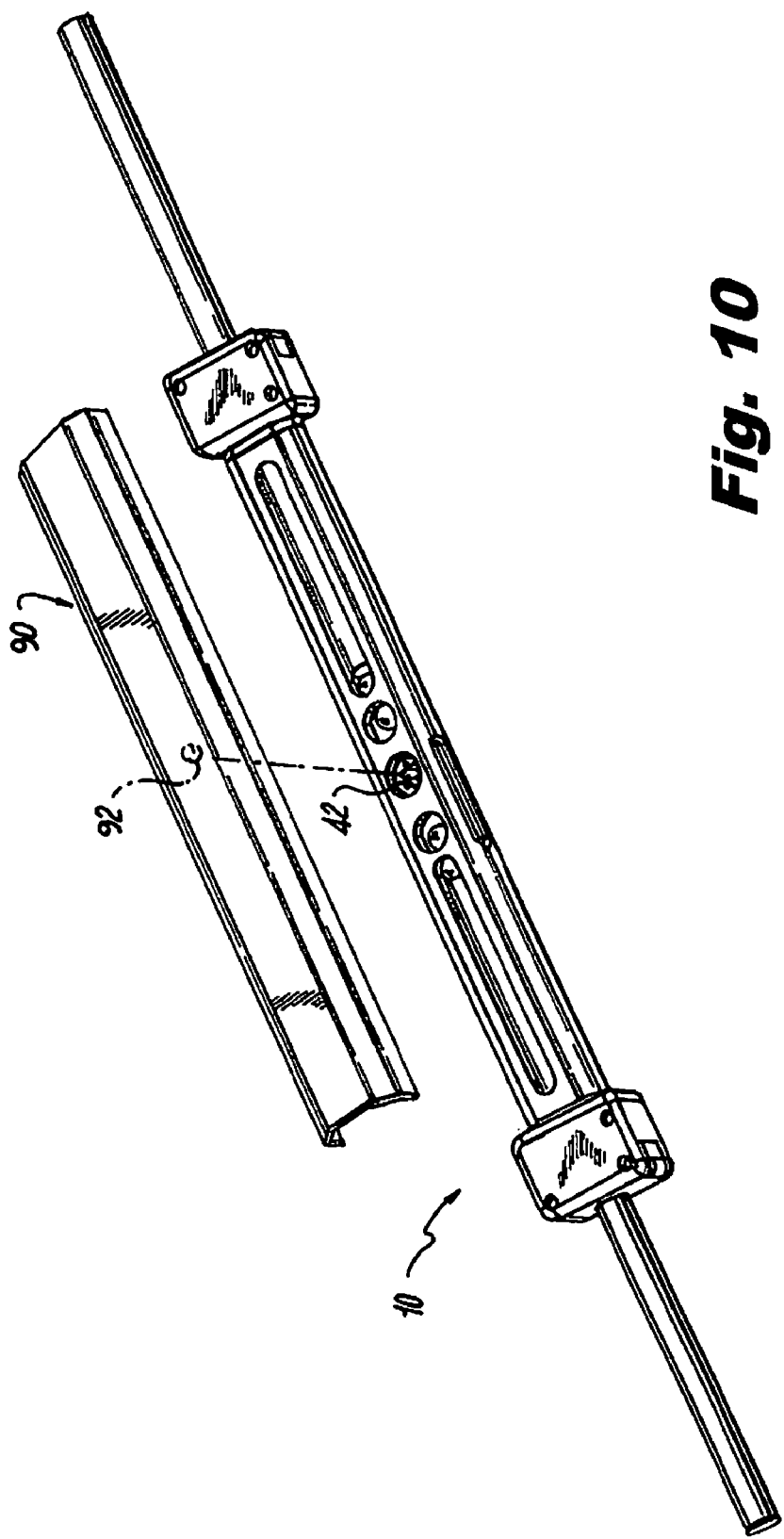
FIG. 10 a top perspective view of the forced growth axial growing spine device of FIGS. 1-8 with the a cover.

In another embodiment, as shown in FIG. 10, the axial growth device 10 contains a cover plate 90, which prevents any access or in-growth of tissue along the length of the axial growth device 10. In addition, the cover plate 90 may also provide a locking mechanism 92. The locking mechanism 92 may interface with a hex drive 42 in the camming mechanism 50 to prevent the camming mechanism 50 from rotating.

Figure 11:
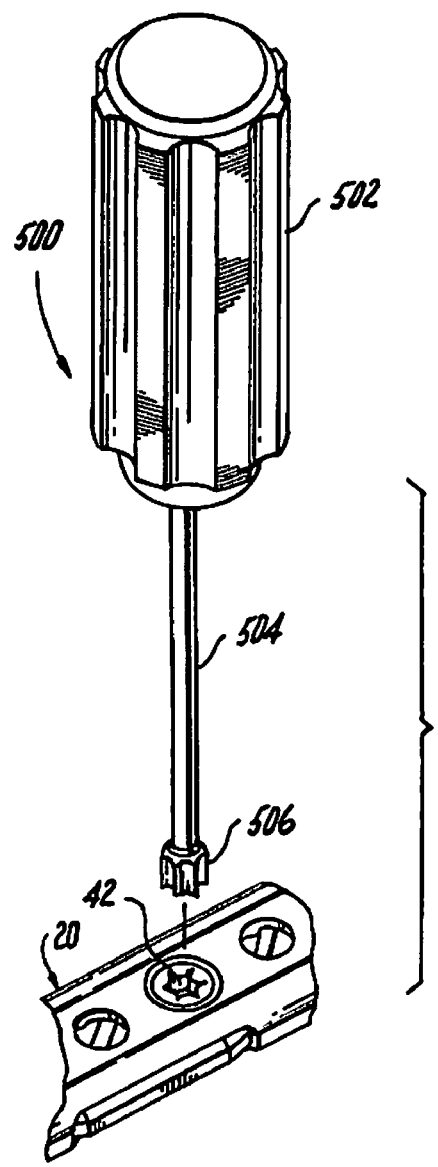
FIG. 11 is a perspective view of a tool used to rotate a cam in the forced growth axial growing spine device.

As shown in FIG. 11, a tool 500 may be used to manually rotate the camming mechanism 50 via the hex drive 42. The tool 500 includes a handle 502, a shaft 504, and a hex drive head 506. The hex drive head 506 is shaped and sized to be slightly smaller and to fit into the hex drive 42. As a result, a user or physician may manually turn the tool 500 to open and close the camming mechanism 50.

Figure 12:
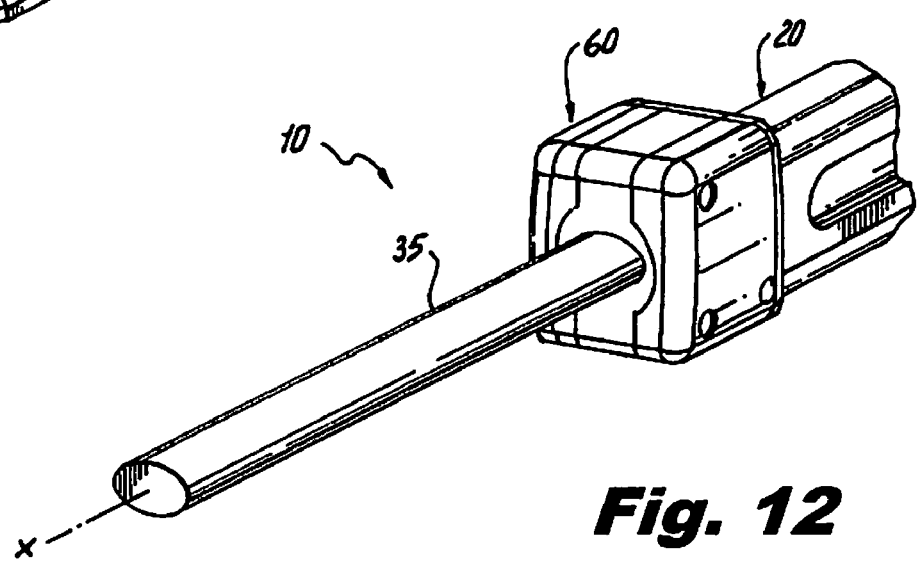
FIG. 12 is a perspective view of the forced growth axial growing spine device having a spinal rod with a non-circular cross-section.

In a further embodiment, as shown in FIG. 12, the spinal rod 35 may have a non-circular cross-section. While a round cross-section is desirable, a spinal rod 35 having at least one portion that is flat along its length, or at least narrower along one radial direction, would prevent the spinal rod 35 from rotating about its longitudinal axis 'x'-'x', while in the axial growth device 10. Additionally, it is contemplated that each spinal rod 35 may include a notch near an end of the spinal rod 35 to inhibit the rod from separating from the axial growth device 10. This rotation may occur in the axial growth device 10 even when the construct length is held constant. Inhibiting rotation of the spinal rod 35 about its longitudinal axis 'x'-'x' is important in preventing the rotation of the spine otherwise known as the "crankshaft" phenomena.

The axial growth device 10 according to the present disclosure is contemplated as a bilateral axial growth device but may be used unilaterally. Furthermore, at least one of said axial growth device 10 may be used unilaterally, in order to build a construct. The spinal rod 30 may be inhibited from translating with respect to a pedicle screw 40, by using a split sleeve device or bushing (not shown for clarity). The axial growth device 10 as disclosed herein may be used in any segment where the spinal rod 30 translation is desired. When using more than one device 10 on a side of the spine, the patient is capable of segmental growth. In other words, placement of the axial growth device 10 between pedicle screws 40 will allow the patient's spine to grow along that segment.

In still another embodiment, the disclosed axial growth device 10 may be used in areas other than the spine such as in long bones. In these applications, the axial growth device 10 may be used internally or externally, and provide the necessary stabilization of the anatomy while still allowing bone growth to continue. Since the axial growth device 10 passively accounts for normal bone growth, additional procedures and manipulation by an operator or the patient are not necessary. Additionally, the axial growth device 10 allows for manual growth to allow a surgeon to force growth of the spinal segment or long bone, which may promote skeletal growth.

Several methods for implantation of the axial growth device 10 are contemplated. In one embodiment, the axial growth device 10 may be used singly at the top, middle, or bottom of a construct, unilaterally or bilaterally. Alternatively, incremental segmental spine growth may be achieved by attaching the axial growth device 10 to more than one bone anchor and rigidly attaching the spinal rod 30 to at least one bone anchor.

In use, an incision is made along the patients bone structure. The axial growth device 10 is provided along with at least two pedicle screws 40. The pedicle screws 40 are placed within the patients vertebrae. The distance between the vertebrae may then be lengthened. The vertebrae may also be realigned to allow placement of the spinal rods 30 within the pedicle screws 40. The axial growth device 10, with spinal rods 30, are placed within the pedicle screws 40 and secured to the pedicle screws. The distance between the vertebrae may then be adjusted again, during both the initial procedure and in subsequent procedures, as described above.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention, and should not be construed to limit the scope thereof.

What is claimed is:

1. A forced growth axial growing spine device comprising:
   a central body portion having opposing ends, the central body portion includes a cam and a pair of ball bearings and defines a pair of ports, one of the pair of ball bearings being located within each port;
   at least one housing disposed at one end of the central body portion, the at least one housing includes a locking mechanism;
   at least one rigid member being movably coupled to the central body portion, the locking mechanism allowing the rigid member to translate in a first direction and inhibit translation of the rigid member in an opposing direction.

2. An expandable spine device, the expandable spine device comprising:
   a central housing including:
      an elongate body having a first end and a second end defining a longitudinal axis therebetween;
      a camming mechanism rotatably attached within the elongate body; and a ring plate located in one of the first and the second ends; and a spinal rod extending from the central housing parallel to the longitudinal axis and operatively coupled to the ring plate, the camming mechanism is operatively connected with the spinal rod to provide a force to the spinal rod in an outwardly direction.

3. The expandable spine device according to claim 2, wherein the camming mechanism has a shape of a diamond.

4. The expandable spine device according to claim 2, further comprising at least a pair of ball bearings, wherein each ball bearing is located between the camming mechanism and one of the spinal rods.

5. The expandable spine device according to claim 2, wherein each of the ring plates defines a passage, the passage allows one of the spinal rods to translate therethrough.

6. The expandable spine device according to claim 2, further comprising a cover plate for restricting access along the elongate body.

7. The expandable spine device according to claim 6, wherein the cover plate provides a locking mechanism for preventing rotation of the camming mechanism.

8. The expandable spine device according to claim 2, further comprising a key mechanism operatively connected with the camming mechanism.

9. The expandable spine device according to claim 8, wherein the key mechanism includes a shaped recess in the camming mechanism.

10. The expandable spine device according to claim 6, wherein the key mechanism defines a hexalobular recess.

11. The expandable spine device according to claim 2, further comprising a locking mechanism, the locking mechanism allows the spinal rods to progress out from the central housing and prevents the spinal rods from retreating into the central housing.

12. An expandable spine device, the expandable spine device comprising:

a central housing;

an expansion control mechanism having a rotatable cam;

a spinal rod extending from the central housing, the expansion control mechanism is operatively connected with the spinal rod to provide a force to the spinal rods in an outwardly direction; and a ball bearing, wherein the ball bearing is located between the expansion control mechanism and the spinal rod.

13. The expandable spine device according to claim 12, wherein the expansion control mechanism being operatively coupled to a key mechanism, the key mechanism defining an axis of rotation.

14. The expandable spine device according to claim 13, wherein the key mechanism is a shaped recess in the expansion control mechanism.

15. The expandable spine device according to claim 13, wherein the key mechanism defines a hexalobular recess.

16. The expandable spine device according to claim 12, further comprising a locking mechanism, the locking mechanism allows the spinal rod to progress out from the central housing and prevents the spinal rod from retreating into the central housing.

17. An expandable spine device, the expandable spine device comprising:

a central housing;

an expansion control mechanism having a rotatable cam;

a spinal rod extending, from the central housing, the expansion control mechanism is operatively connected with the spinal rod to provide a force to the spinal rods in an outwardly direction; and a ring plate, the ring plate defining a passage for receiving the spinal rod.

18. An expandable spine device, the expandable spine device comprising:

a central housing;

an expansion control mechanism having a rotatable cam;

a spinal rod extending from the central housing, the expansion control mechanism is operatively connected with the spinal rod to provide a force to the spinal rods in an outwardly direction; and a cover plate for restricting access along the central housing.

19. The expandable spine device according to claim 18, wherein the cover plate provides a locking mechanism for preventing rotation of the expansion control mechanism.

* * * * *